United States Patent [19]
Allen

[11] Patent Number: 5,636,456
[45] Date of Patent: Jun. 10, 1997

[54] ORTHOPEDIC APPARATUS AND FOOTWEAR FOR REDISTRIBUTING WEIGHT ON FOOT

[76] Inventor: Don T. Allen, 4406 Oxford Way, Norman, Okla. 73072

[21] Appl. No.: 367,425

[22] Filed: Dec. 30, 1994

[51] Int. Cl.$^6$ .................. A61F 5/14; A43B 13/38
[52] U.S. Cl. .................. 36/168; 36/166; 36/91; 36/27
[58] Field of Search .................. 36/155–158, 168, 36/166, 171, 175, 177, 179, 107, 108, 76 R, 27, 82, 91, 75 R

[56] References Cited

U.S. PATENT DOCUMENTS

| | | |
|---|---|---|
| 1,102,343 | 7/1914 | Kovacs . |
| 1,625,048 | 4/1927 | Nock . |
| 1,644,762 | 10/1927 | Voll .................. 36/157 |
| 1,657,367 | 1/1928 | Brownell .................. 36/155 |
| 1,686,034 | 10/1928 | Roser .................. 36/161 |
| 1,699,883 | 1/1929 | Fosmoe .................. 36/155 |
| 1,885,259 | 11/1932 | Hirschfield .................. 36/156 |
| 2,050,006 | 8/1936 | Heuer .................. 36/156 |
| 2,142,839 | 1/1939 | Flint .................. 36/171 |
| 2,428,244 | 9/1947 | Roles .................. 36/168 |
| 2,447,603 | 8/1948 | Snyder . |
| 2,508,318 | 5/1950 | Wallach . |
| 2,548,308 | 4/1951 | Hensley . |
| 3,667,473 | 6/1972 | Matteson .................. 36/157 |
| 3,886,674 | 6/1975 | Pavia . |
| 4,492,046 | 1/1985 | Kosova . |
| 4,534,124 | 8/1985 | Schnell . |
| 4,566,206 | 1/1986 | Weber . |
| 4,592,153 | 6/1986 | Jacinto . |
| 4,771,554 | 9/1988 | Hannemann . |
| 4,941,272 | 7/1990 | Allen . |
| 5,159,767 | 11/1992 | Allen . |
| 5,203,095 | 4/1993 | Allen . |

FOREIGN PATENT DOCUMENTS

| | | |
|---|---|---|
| 1169599 | 7/1985 | U.S.S.R. . |
| 80/00781 | 5/1980 | WIPO . |

*Primary Examiner*—Ted Kavanaugh
*Attorney, Agent, or Firm*—Wigman, Cohen, Leitner & Myers, P.C.

[57] ABSTRACT

An orthopedic apparatus and footwear for distributing weight evenly so as to relieve pressure and discomfort from the ball, arch and heel region of the wearer's foot. This is accomplished by first and second embodiments in which two substantially parallel plates are mounted between an inner sole and an outer sole. The parallel plates are spaced apart by a spacer which is located at a point or region of attachment between the two plates in the arch region of the footwear. The lower plate is rigid and the upper plate is flexible. A layer of easily deformable foam material is provided between the two plates. In the first embodiment, sole spacers are provided in the toe region of the footwear. As a result of the attachment configuration, the plates are cantilever mounted both extending forward and rearward from the arch region. In operation, the flexing of the forward cantilever portion of the flexible plate relative to the rigid plate cushions the ball region and redistributes weight rearward from the ball of the foot and the flexing of the rearward cantilever portion of the flexible plate relative to the rigid plate cushions the heel region and redistributes weight forward from the heel of the foot. A third embodiment also uses a flexible plate and a rigid plate which are attached at an acute angle in the arch region and extend forward toward the ball region. A wedge is provided between the two plates. The flexing of the flexible plate relative to the rigid plate cushions the ball region and redistributes weight rearward from the ball of the foot. The first and second embodiments can be modified as in the third embodiment to provide parallel plates which only extend forward from the arch region, with spacers provided in the rearward region behind the arch.

36 Claims, 3 Drawing Sheets

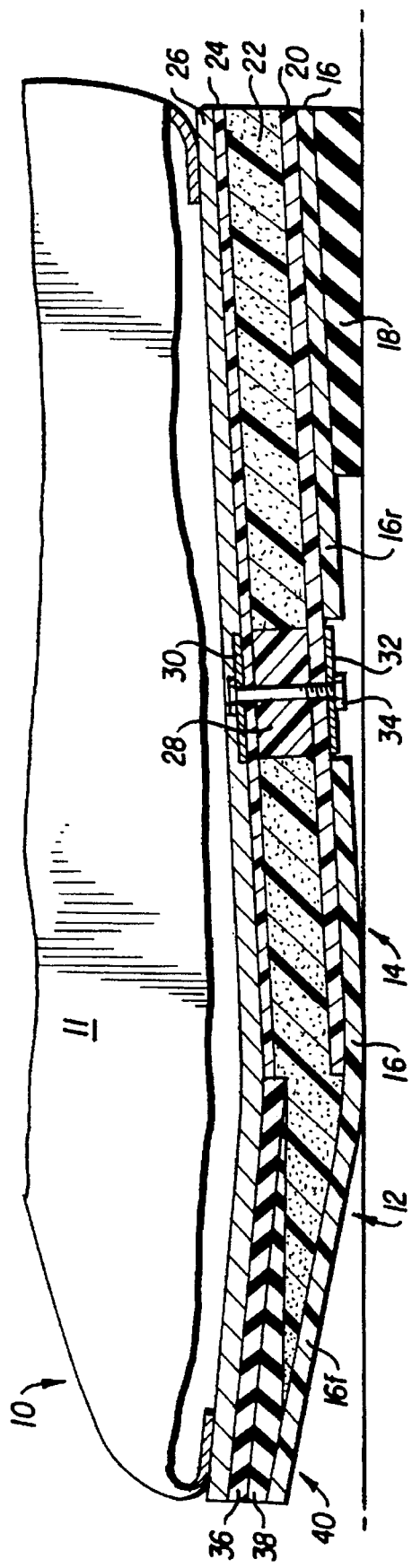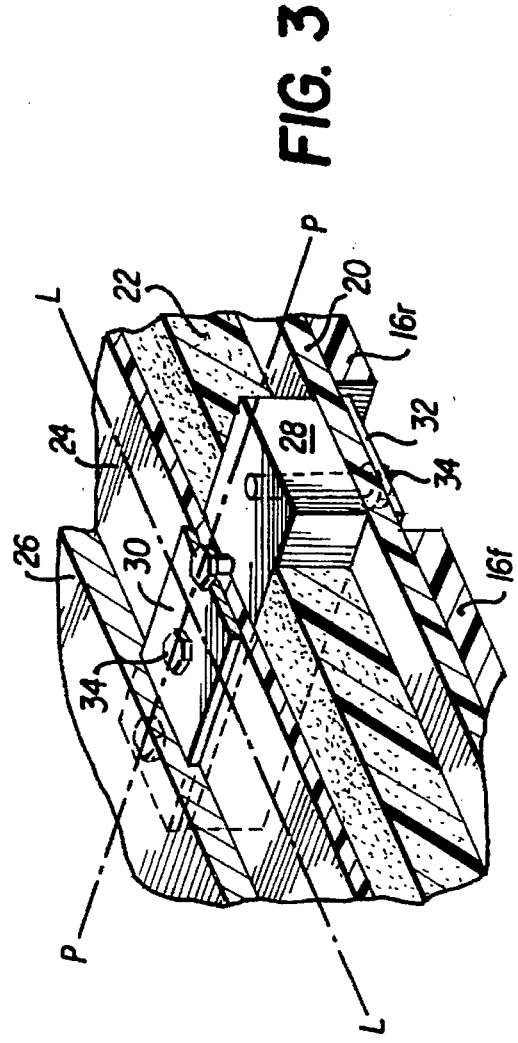

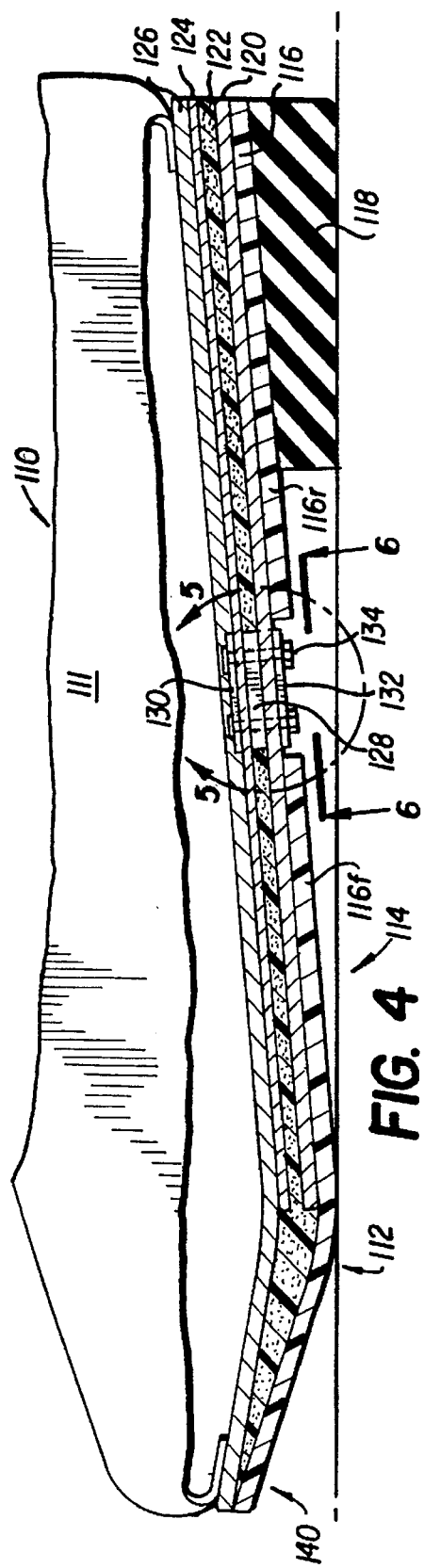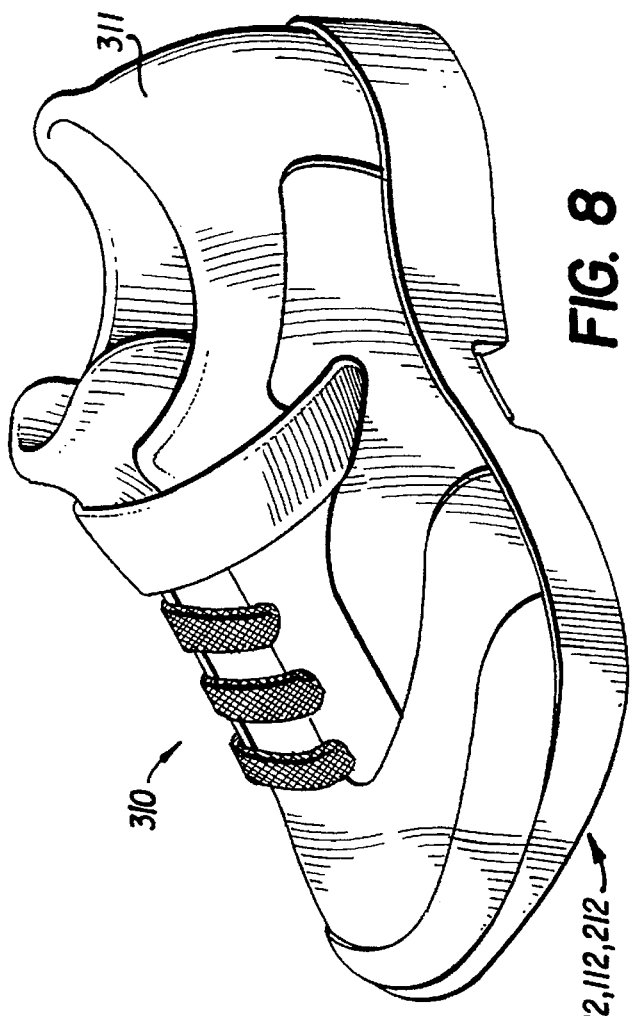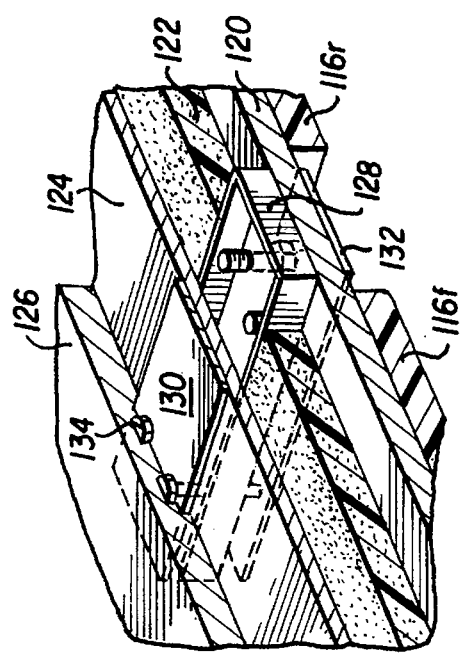

ORTHOPEDIC APPARATUS AND FOOTWEAR FOR REDISTRIBUTING WEIGHT ON FOOT

BACKGROUND OF THE INVENTION

1. Field of the Invention

The present invention is directed to shoes or footwear worn by humankind, and more particularly to the support the shoes or footwear provide for the foot.

2. Description of the Prior Art

Problems with the foot, especially the condition known as "fallen arches" have been addressed in various shoe or footwear constructions. Included among these are two patents issued to the present inventor, U.S. Pat. Nos. 5,159,767 and 5,203,095. The disclosures of each of these patents are hereby incorporated by reference herein. The emphasis in these prior art patents and in the other prior art embodiments known to the inventor are directed to providing relief by distributing weight from the arch toward the ball of the foot and also away from the heel.

For example, in the inventor's prior art patents, the embodiments were directed to an orthopedic apparatus and shoe incorporating the apparatus including a structure which cooperates to distribute weight from the arch area and heel of the foot toward the ball of the foot. This is accomplished by a combination of rigid and flexible members which cooperate with each other and the foot of the wearer. More particularly, in first and second embodiments, a first rigid reinforcing member is disposed inside of the shoe and located under the arch region of the foot and extends in the direction of the ball of the foot. A flexible supporting member is attached to the bottom of the shoe. A second rigid mounting member extends at an acute angle from the flexible member with the apex at the arch region back toward the heel region and forms the base for mounting of the heel to the shoe if a heel is to be provided. The flexible member, the second rigid member and the inside first rigid member are commonly attached by fasteners such as bolts or pop rivets in the arch region. The result is a pivot axis substantially transverse to the longitudinal axis of the shoe. The flexible member functions as a spring plate which is compressed toward the second rigid member. This serves to support and cushion the heel region of the foot. The first rigid member, extending forwardly toward the ball of the foot, in cooperation with the flexible spring member and second rigid member, serves to provide arch support and to distribute weight over the length of the foot.

In a third embodiment of the prior art orthopedic apparatus by the same inventor, the first rigid reinforcing member is eliminated from the inside of the shoe and replaced by a rigid reinforcing member in the form of a sole wedge which is disposed forward of the apex formed by the acute-angle connected mounting member and supporting member. The acute angle is maintained by a wedge disposed between the mounting member and supporting member. In the third embodiment, the apparatus is attached or bonded to an inner sole and an outer sole is placed over the orthopedic apparatus and bonded to the apparatus and the inner sole. A heel, also bonded to the apparatus, can be provided, or, alternatively, the heel can be eliminated.

In the second and third embodiments, a reinforced resin is used to provide either a flexible plate or a substantially rigid plate, depending upon the number of laminations of vinyl ester resin and graphite fabric employed.

The above corrective measures, while highly effective in addressing fallen arches, do not in themselves address problems people have in the ball of the foot. Therefore, it would be desirable to provide an orthopedic stabilizer attachment or sole design which distributes weight away from the ball of the foot toward the arch and/or the heel of the foot, thereby more evenly distributing the wearer's weight to alleviate pain or discomfort in the ball region, as well as in other regions of the foot.

SUMMARY OF THE INVENTION

Unlike the prior art orthopedic devices, the present invention is directed toward distributing weight evenly so as to relieve pressure and discomfort from the ball region of the shoe wearer's foot, as well as other regions of the foot. This is accomplished by first and second embodiments in which two substantially parallel plates are mounted between an inner sole and an outer sole. The parallel plates are spaced apart by a spacer which is located at a point or region of attachment between the two plates in the arch region of the shoe. The attachment point or area forms a pivot axis substantially transverse to the longitudinal axis of the shoe. The lower plate is rigid and the upper plate is flexible. A layer of easily deformable foam material is provided between the two plates. In the first embodiment, sole spacers are provided in the toe region of the shoe. As a result of the attachment configuration, the plates are cantilever mounted both extending forward and rearward from the arch region. In operation, during walking, running or standing, the flexing of the flexible plate relative to the rigid plate forward of the pivot axis cushions the ball region and the flexible plate redistributes weight away from the ball of the foot to the arch and heel of the foot. Similarly, the flexing of the flexible plate relative to the rigid plate rearward of the pivot axis cushions the heel region and the flexible plate redistributes weight away from the heel to the arch and ball of the foot.

A third embodiment also uses a flexible plate and a rigid plate which are attached at an acute angle in the arch region and extend forward toward the ball region. A wedge is provided between the two plates. The flexing of the flexible plate relative to the rigid plate redistributes weight away from the ball of the foot to the arch and heel of the foot.

The first and second embodiments can be modified as in the third embodiment to provide parallel plates which only extend forward from the arch region, with spacers provided in the rearward region behind the arch.

With the foregoing and other advantages and features of the invention that will become hereinafter apparent, the nature of the invention may be more clearly understood by reference to the following detailed description of the invention, the appended claims and to the several views illustrated in the attached drawings.

BRIEF DESCRIPTION OF THE DRAWINGS

FIG. 2 is a sectional view taken along line 2—2 of FIG. 1;

FIG. 3 is a sectional detail view of a support attachment of the first embodiment;

FIG. 4 is a sectional view of a second embodiment of orthopedic footwear in the form of a shoe in accordance with the present invention;

FIG. 5 is a sectional detail view of a support attachment of the second embodiment taken along detail line 5—5 of FIG. 4;

FIG. 8 is a perspective view of orthopedic footwear in the form of an athletic shoe in accordance with the present invention.

DETAILED DESCRIPTION OF THE INVENTION

Figure 1:
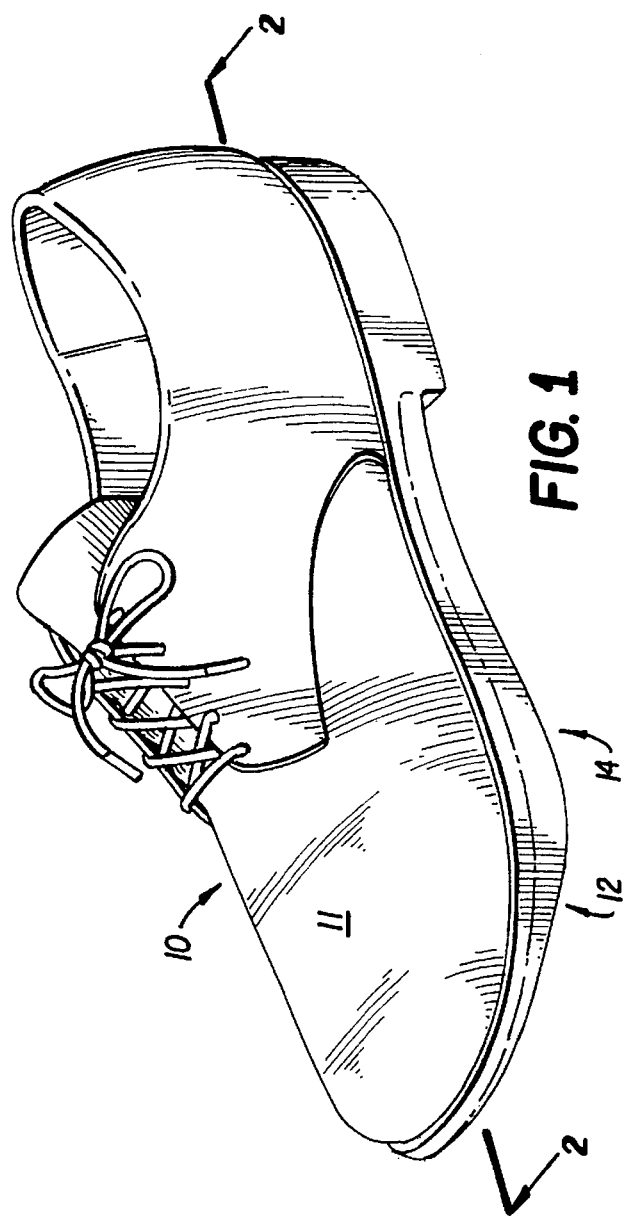
FIG. 1 is a perspective view of a first embodiment of orthopedic footwear in the form of a shoe in accordance with the present invention.

Referring now to the drawings, wherein like elements are designated by like numerals, FIGS. 1–3 show a first preferred embodiment of footwear in the form of an orthopedic shoe, designated generally by the numeral 10, in accordance with the invention.

FIG. 1 shows a perspective view of orthopedic footwear in the form of a dress shoe 10 having upper portion 11 and having an orthopedic apparatus 12 incorporated in the sole structure 14 of the shoe 10. FIG. 2 is a sectional view of shoe 10, showing the various components which make up the orthopedic apparatus 12 of the shoe 10. Orthopedic apparatus 12 is comprised of a grouping of plates which have support and flexing properties and which cooperate to distribute a wearer's weight over the foot to relieve the wearer of discomfort due to various orthopedic maladies. Orthopedic apparatus 12 includes an outer sole 16 in two parts, front portion 16f and rear portion 16r. A heel 18 is attached to rear portion 16r. A rigid lower stabilizer plate 20 is provided, to which sole 16 is attached. Flexible foam layer 22 is provided above lower plate 20. Flexible upper spring plate 24 is provided above foam layer 22. Upper (inner) sole 26 is provided above upper plate 24. Spacer block 28 is provided between upper plate 24 and lower plate 20. Upper plate 24 and lower plate 20 are held together between upper and lower fastened fastener plates 30, 32 by a plurality (preferably four) fasteners 34. Upper sole spacer 36 and lower sole spacer 38 are provided at the toe 40 of the shoe 10. Lower sole spacer 38 is wedge-shaped at both the front and rear. Outer sole 16 is fastened at the toe to lower sole spacer 38, which is fastened to upper sole spacer 36, which is in turn fastened to upper (inner) sole 26.

FIG. 3 shows spacer block 28 and fasteners 34 which cooperate with upper plate 24 and lower plate 20 to form a pivot region or axis P transverse to the longitudinal axis L of shoe 10.

Orthopedic apparatus 12 and sole structure 14 are made of materials having suitable flexing characteristics as well as suitable wear characteristics. Sole 16 is typically made of nylon shoe material or shoe leather. Heel 18 is typically made of nylon or leather. Rigid lower stabilizer plate 20 is preferably made of a carbon graphite material. Flexible upper spring plate 24 is also preferably made of a carbon graphite material, but lower plate 20 is preferably 30% thicker than upper plate 24. The carbon graphite material of plates 20, 24 is a resin reinforced and laminated with layers of a carbon graphite fabric. Specifically, the resin is preferably DERAKANE 8084 resin, a vinyl ester resin manufactured by Dow Chemical Company, using approximately 2.5 weight percent methyl ethyl ketone peroxide as a catalyst, approximately 0.40 weight percent cobalt naphthenate as a promoter, and approximately 0.10 weight percent dimethylaniline as an accelerator. The resin is laminated with layers of Hexcel Corporation Hexcel GA130 carbon graphite fabric, 15 mils thick, 14×4 count, 13 oz/sq. yd., 12k carbon fusible yarn type, having plain heatset weave. The lower plate 20 is made with 6 layers of the carbon graphite fabric and has an overall thickness of 0.215 inch. The upper plate 24 is made with 4 layers of the carbon graphite fabric and has an overall thickness of 0.160 inch. Upper plate 24 and lower plate 20 are typically approximately 8 inches long for a standard size 9 ½ men's shoe. Heel 18, sole 16, and upper and lower plates 24, 20 are shaped and sized in conformity to the shoe size. Spacer block 28 is rectangular and typically made from bi-directional carbon graphite fibers and fiberglass resin and has dimensions of 1 inch×3 inch×⅜ inch thickness. Plates 30, 32 are typically made from 6 AL/4 V grade titanium and are rectangular, having dimensions of 1 inch×3 inch×0.040 inch thickness. The widths of spacer block 28, plates 30, 32, sole 16 and other components can be varied to match the width of the shoe, depending upon the width of upper sole 26. In addition, the dimension of spacer block 28 in the direction of the longitudinal axis of the shoe can be increased from approximately 1 inch to 3 inches to provide further stiffness of upper plate 24. Similarly, the thickness of spacer block 28 can be chosen to be of a suitable dimension, as for example, in the range of ⅛ to 2 inches. Such increased stiffness would be beneficial to a heavy wearer of the shoe and also to a runner or jogger in an athletic shoe equipped with the orthopedic apparatus 12. Fasteners 34 are typically nut and bolt combinations, made of titanium or stainless steel. Rivets can also be used in place of bolts. It is contemplated that other mechanical fasteners, as well as adhesive fasteners can be used. Sole spacers 36, 38 are typically made of crepe sole material. The various layers are adhesively attached using adhesives known in the shoe art. Alternatively, the layers can be attached mechanically using suitable fasteners.

To reduce weight, it is contemplated that the sole 16 can be made of a laminated crepe material with an outer layer of 200 grit abrasion nylon material. Crepe material can be inserted between the heel 18 and the bottom of plate 20. Alternatively, a ¼ inch crepe sole may be used.

Orthopedic apparatus 12 can be constructed as part of an entirely new shoe. Alternatively, orthopedic apparatus 12 can be made separately and attached to the bottom of the original sole of an existing shoe, corresponding to upper sole 26.

In operation, the two plates 20, 24 are mounted essentially parallel to each other over their respective lengths and in cantilever fashion at the point or region of attachment in the arch region of the shoe. As a result of the differential thickness between the upper plate 24 and the lower plate 20, the upper plate 24 tends to flex toward the lower plate 20 about transverse pivot axis P (FIG. 3) during the weight shifts which occur when a wearer of the shoe stands, walks or turns. As a result, there is a redistribution of the weight along the shoe. The flexing of flexible upper plate 24 cantilever portion forward of the attachment region or pivot axis P cushions the ball region and the flexible upper plate 24 redistributes weight away from the ball of the foot toward the arch and heel, thereby relieving discomfort in that region of the foot. Similarly, the flexing of flexible upper plate 24 cantilever portion rearward of the attachment region or pivot axis P cushions the heel region and the flexible upper plate 24 redistributes weight away from the heel of the foot toward the arch and ball, thereby relieving discomfort in that region of the foot.

As shown in FIG. 2, plates 20 and 24 extend over approximately 8 inches in a typical size 9 ½ men's shoe. It is contemplated to eliminate the rearward extending portions of the plates 20 and 24 and provide spacers between the heel 18, sole 16r and sole 26. This will result in weight redistribution only from the ball region back toward the arch and heel regions.

Figure 6:
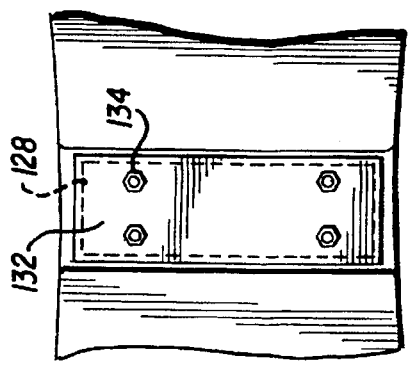
FIG. 6 is a plan view of a support attachment of the second embodiment taken along line 6—6 of FIG. 4.

FIGS. 4–6 illustrate a second embodiment of a shoe 110, similar to the first embodiment, with the exception of the elimination of sole spacers at the toe of the shoe 110, and a different fastening structure located at the arch area of the shoe 110. Similar elements are designated with similar numerals incremented by 100. As in the first embodiment, the shoe 110 has an upper portion 111 and an orthopedic structure 112 incorporated in sole structure 114. Orthopedic apparatus 112 includes outer sole 116 in two parts, front portion 116f and rear portion 116r. Heel 118 is attached to rear sole portion 116r. Rigid lower plate 120 is provided to which sole 116 is attached. Flexible foam layer 122 is provided above lower plate 120. Flexible upper plate 124 is provided above foam layer 122. A spacer box 128 is provided between upper plate 124 and lower plate 120, rather than the spacer block 28 of the first embodiment. Upper plate 124 and lower plate 120 are held between upper and lower fastener plates 130, 132 fastened together by a plurality (preferably four) of bolts or fasteners 134 which pass through the hollow center of and are located at the corners of spacer box 128. Upper sole 126 and outer sole 116 are fastened together by adhesive or by mechanical fasteners at the tip of the toe area 140.

The materials of the embodiment of FIGS. 4–6 are similar to those of the embodiment of FIGS. 1–3, with the exception that spacer block 28 is replaced by a hollow aluminum spacer box 128. Spacer box 128 is typically rectangular, having dimensions of 3 inch×1 inch×⅜ inch in thickness (height) for a size 9 ½ men's shoe. The dimensions of the spacer box 128 vary in accordance with shoe size. Similarly, the thickness (height) of spacer box 128 can be chosen to be of a suitable dimension, as for example, in the range of ⅛ to 2 inches.

The operation of the embodiment of FIGS. 4–6 is also substantially the same as the embodiment of FIGS. 1–3, with the exception that the sole spacers 36, 38 are eliminated. As a result, the toe region is thinner. Also, it is contemplated that plates 120 and 124 can be shortened to extend only forward toward the ball of the foot with spacers provided between heel 118, sole 116r and sole 126.

Figure 7:
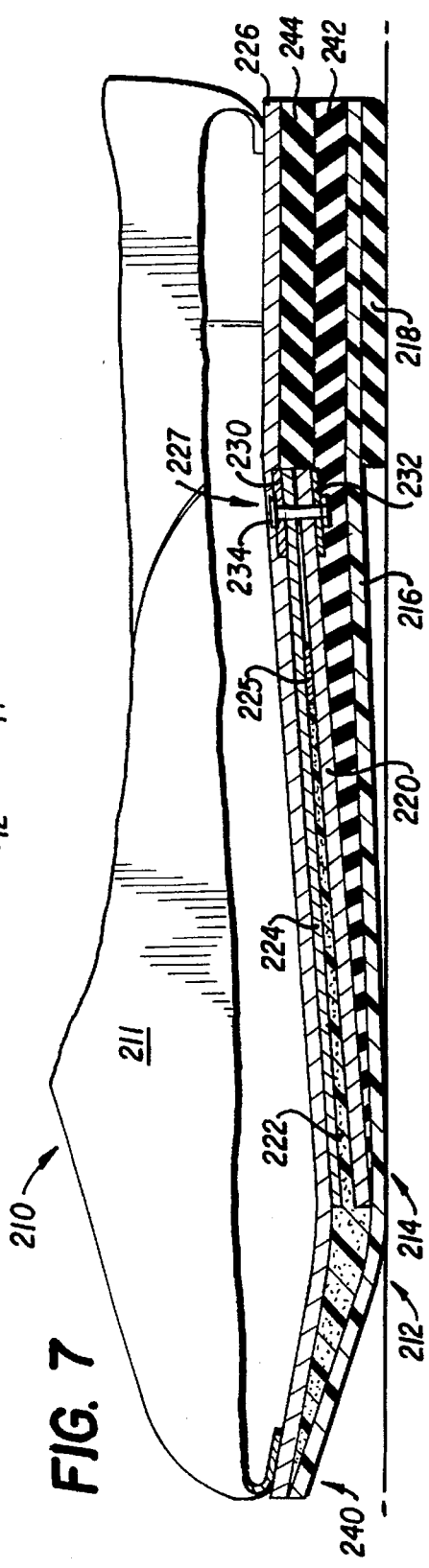
FIG. 7 is a sectional view of a third embodiment of orthopedic footwear in the form of a shoe in accordance with the present invention.

FIG. 7 illustrates a third embodiment of a shoe 210 in accordance with the invention. Like components have similar numerals to the first embodiment, incremented by 200. Therein, a shoe 210 is shown having upper portion 211 and having an orthopedic structure 212 incorporated in sole structure 214 of shoe 210. Orthopedic apparatus 212 is comprised of outer sole 216 with heel 218 attached thereto. A rigid lower plate 220 is attached to a flexible upper plate 224. A flexible foam layer 222 is interposed between upper and lower plates 224, 220. A wedge 225 is interposed between upper and lower plates 224, 220. Upper and lower plates 224, 220 are joined together at an apex 227 formed by a plurality of fasteners 234 through plates 230, 232. The apex 227 is located in the arch region of the shoe 210. Wedge 225 is located approximately 1 inch in from of apex 227. Rubber inserts 242, 244 are provided between lower sole 216 and upper sole 226. Upper sole 226 and lower sole 216 are attached adhesively or mechanically at the toe region 240 of the shoe.

The materials of the embodiment of FIG. 7 are similar to those of FIGS. 1–3. Wedge 225 is a wedge-shaped carbon graphite resin insert. The operation of the embodiment of FIG. 7 is similar to that of the other embodiments except that only weight forward of the arch area is redistributed by flexing of the upper plate 224 and the rigid lower plate 220 to relieve discomfort in the ball region of the wearer's foot.

FIG. 8 illustrates a sports or athletic shoe 310 which can incorporate any one of the orthopedic structures 12, 112 or 212 described herein.

Although shoes have been described in particular, it is contemplated that orthopedic structures 12, 112 or 212 can be incorporated in any footwear, including shoes, boots, sandals, sneakers or athletic footwear.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

I claim:

1. An orthopedic apparatus for use on footwear having a sole portion, said orthopedic apparatus comprising a region corresponding to the heel of a human foot, a region corresponding to the arch of a human foot, and a region corresponding to the ball of a human foot, said apparatus comprising:

a substantially rigid lower first member extending from the arch region forward toward the ball region;

a substantially flexible upper supporting member extending from the arch region forward toward the ball region;

a fastener means, located in said arch region, for fastening said first member and said supporting member together;

a spacer, for maintaining a separation between said upper supporting member and said lower first member, said lower first member and said upper supporting member being substantially parallel and cantilever mounted at said spacer so as to distribute weight rearward from the ball region toward the arch region and the heel region and whereby said upper supporting member flexes toward said lower first member to thereby cushion the ball region.

2. An orthopedic apparatus as in claim 1, wherein said substantially rigid first member is a rigid carbon graphite plate.

3. An orthopedic apparatus as in claim 1, wherein said substantially flexible supporting member is a flexible carbon graphite plate.

4. An orthopedic apparatus as in claim 1, wherein said fastener means comprises at least one bolt.

5. An orthopedic apparatus as in claim 1, further comprising a heel mounted on said sole portion in the region corresponding to the heel of the human foot.

6. An orthopedic apparatus as in claim 1, wherein said spacer is made of a carbon graphite material.

7. An orthopedic apparatus as in claim 1, wherein said spacer is located in the arch region of the footwear.

8. An orthopedic apparatus as in claim 1, wherein said first rigid member and said flexible supporting member are each planar and substantially parallel.

9. An orthopedic apparatus as in claim 1, wherein said first rigid member and said flexible supporting member extend rearwardly toward said heel region.

10. Orthopedic footwear comprising:

an upper portion for encompassing a human foot, and a sole portion, said portions forming a region corresponding to the heel of a human foot, a region corresponding to the arch of a human foot, and a region corresponding to the ball of a human foot;

a substantially rigid lower first member extending from the arch region forward toward the ball region;

a substantially flexible upper supporting member extending from the arch region toward the ball region;

a fastener means, located in said arch region, for fastening said first member and said supporting member together;

a spacer for maintaining a separation between said upper supporting member and said lower first member;

said lower first member and said upper supporting member being substantially parallel and cantilever mounted at said spacer so as to distribute weight rearward from the ball region toward the arch region and the heel region and whereby said upper supporting member flexes toward said lower first member to thereby cushion the ball region.

11. Orthopedic footwear as in claim 10, wherein said substantially rigid first member is a rigid carbon graphite plate.

12. Orthopedic footwear as in claim 10, wherein said substantially flexible supporting member is a flexible carbon graphite plate.

13. Orthopedic footwear as in claim 10, wherein said fastener means comprises at least one bolt.

14. Orthopedic footwear as in claim 10, further comprising a heel mounted on said sole portion in the region corresponding to the heel of the human foot.

15. Orthopedic footwear as in claim 10, wherein said spacer is made of a carbon graphite material.

16. Orthopedic footwear as in claim 10, wherein said spacer is located in the arch region of the footwear.

17. Orthopedic footwear as in claim 10, wherein said first rigid member and said flexible supporting member are each planar and substantially parallel.

18. Orthopedic footwear as in claim 10, wherein said first rigid member and said flexible supporting member extend rearwardly toward said heel region.

19. Orthopedic footwear as in claim 10, wherein said footwear is suitable for a use selected from the group of uses consisting of dress, work, recreational and athletic use.

20. Orthopedic footwear as in claim 10, wherein said fastener means comprises at least one bolt.

21. An orthopedic apparatus for use on footwear having a sole portion, said orthopedic apparatus comprising a region corresponding to the heel of a human foot, a region corresponding to the arch of a human foot, and a region corresponding to the ball of a human foot, said apparatus comprising:

a substantially rigid lower first member extending from the arch region forward toward the ball region and extending rearward from the arch region toward the heel region;

a substantially flexible upper supporting member extending from the arch region forward toward the ball region and extending rearward from the arch region toward the heel region;

a fastener means, located in the arch region, for fastening said first member and said supporting member together;

a spacer, for maintaining a separation between said upper supporting member and said lower first member, said lower first member and said upper supporting member being substantially parallel and cantilever mounted at said spacer so as to distribute weight rearward from the ball region toward the arch region and the heel region and said upper supporting member flexes toward said first member to thereby cushion the ball region, and whereby further said lower first member, said upper supporting member and said spacer cooperate to distribute weight forward from the heel region toward the arch region and the ball region and whereby said upper supporting member flexes toward said lower first member to thereby cushion the heel region.

22. An orthopedic apparatus as in claim 21, wherein said substantially rigid first member is a rigid carbon graphite plate.

23. An orthopedic apparatus as in claim 21, wherein said substantially flexible supporting member is a flexible carbon graphite plate.

24. An orthopedic apparatus as in claim 21, further comprising a heel mounted on said sole portion in the region corresponding to the heel of the human foot.

25. An orthopedic apparatus as in claim 21, wherein said spacer is made of a carbon graphite material.

26. An orthopedic apparatus as in claim 21, wherein said spacer is located in the arch region of the footwear.

27. An orthopedic apparatus as in claim 21, wherein said first rigid member and said flexible supporting member are each planar and substantially parallel.

28. Orthopedic footwear comprising:

an upper portion for encompassing a human foot, and a sole portion, said portions forming a region corresponding to the heel of a human foot, a region corresponding to the arch of a human foot, and a region corresponding to the ball of a human foot;

a substantially rigid lower first member extending from the arch region forward toward the ball region and extending rearward from the arch region toward the heel region;

a substantially flexible upper supporting member extending from the arch region forward toward the ball region and extending rearward from the arch region toward the heel region;

a fastener means, located in said arch region, for fastening said first member and said supporting member together;

a spacer for maintaining a separation between said upper supporting member and said lower first member;

said lower first member and said upper supporting member being substantially parallel and cantilever mounted at said spacer so as to cooperate to distribute weight rearward from the ball region toward the arch region and the heel region and whereby said upper supporting member flexes toward said lower first member to thereby cushion the ball region, and whereby further said lower first member, said upper supporting member and said spacer cooperate to distribute weight forward from the heel region toward the arch region and the ball region and said upper supporting member flexes toward said lower first member to thereby cushion the heel region.

29. Orthopedic footwear as in claim 28, wherein said substantially rigid first member is a rigid carbon graphite plate.

30. Orthopedic footwear as in claim 28, wherein said substantially flexible supporting member is a flexible carbon graphite plate.

31. Orthopedic footwear as in claim 28, wherein said fastener means comprises at least one bolt.

32. Orthopedic footwear as in claim 28, further comprising a heel mounted on said sole portion in the region corresponding to the heel of the human foot.

33. Orthopedic footwear as in claim 28, wherein said spacer is made of a carbon graphite material.

34. Orthopedic footwear as in claim 28, wherein said spacer is located in the arch region of the footwear.

35. Orthopedic footwear as in claim 28, wherein said first rigid member and said flexible supporting member are each planar and substantially parallel.

36. Orthopedic footwear as in claim 10, wherein said footwear is suitable for a use selected from the group of uses consisting of dress, work, recreational and athletic use.

* * * * *